United States Patent [19]

Omori et al.

[11] Patent Number: 4,774,355

[45] Date of Patent: Sep. 27, 1988

[54] PROCESS FOR PREPARING PENTAERYTHRITOL-TETRAKIS(3-ALKYLTHIO-PROPIONATE)

[75] Inventors: Hiroyuki Omori; Teruhiko Ishii; Mitsumasa Kaitoh, all of Mie; Shoichiro Mori, Ibaraki, all of Japan

[73] Assignee: Mitsubishi Petrochemical Co., Ltd., Tokyo, Japan

[21] Appl. No.: 922,726

[22] Filed: Oct. 24, 1986

[51] Int. Cl.$^4$ .................................. C07C 149/20
[52] U.S. Cl. .................................. 560/152
[58] Field of Search .................................. 560/152

[56] References Cited

U.S. PATENT DOCUMENTS 2,828,321  3/1958  Bullock .................. 560/152 X
3,758,549  9/1973  Dexter et al. .................. 560/152
4,125,515  11/1978  Kuczkowski .................. 560/152 X

FOREIGN PATENT DOCUMENTS 54-59225  5/1979  Japan .................. 560/152
55-39249  10/1980  Japan .
55-41654  10/1980  Japan .

Primary Examiner—Michael L. Shippen
Attorney, Agent, or Firm—Oblon, Fisher, Spivak, McClelland & Maier

[57] ABSTRACT

A process for preparing a pentaerythritol-tetrakis(3-alkylthio-propionate) represented by the general formula:

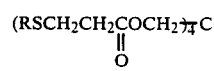

wherein R represents an alkyl group having from 8 to 30 carbon atoms, is disclosed, comprising reacting an alkylmercaptan having from 8 to 30 carbon atoms with an acrylic ester or an acrylic amide to form a 3-alkylthio-propionic acid ester or a 3-alkylthio-propionic acid amide, hydrolyzing the ester or amide to form a 3-alkylthio-propionic acid, and then reacting this product with pentaerythritol. The desired product can easily be obtained at high purity and high yield by this process.

19 Claims, 1 Drawing Sheet

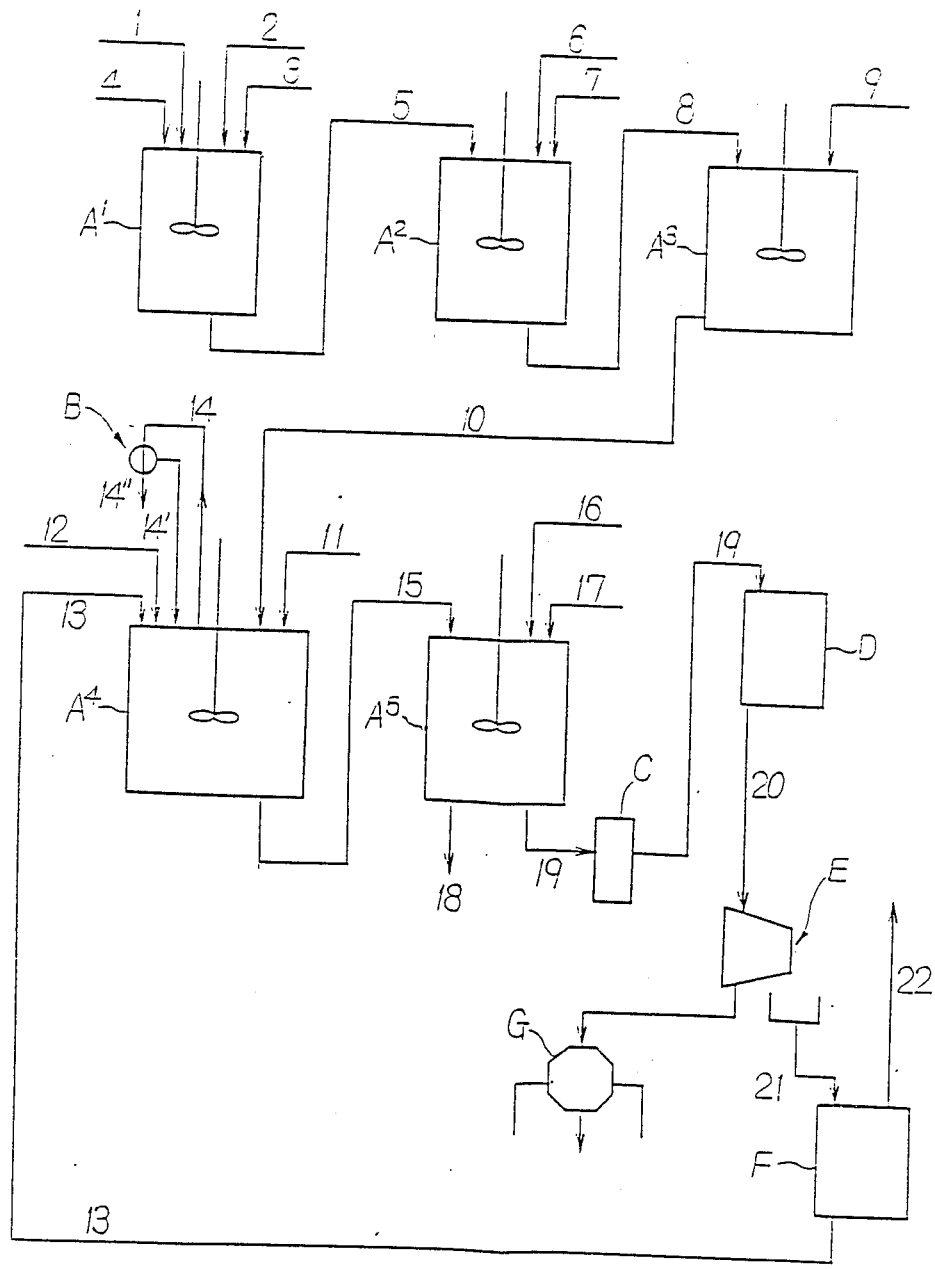

PROCESS FOR PREPARING PENTAERYTHRITOL-TETRAKIS(3-ALKYLTHIO-PROPIONATE)

FIELD OF THE INVENTION

This invention relates to a process for preparing a pentaerythritol-tetrakis(3-alkylthio-propionate).

BACKGROUND OF THE INVENTION

A pentaerythritol-tetrakis(3-alkylthio-propionate) is known to be a modifier or a thermal stabilizer for improving resistance of plastics, e.g., polyolefin resin, ABS resin, etc., to deterioration due to heat or copper in U.S. Pat. No. 3,629,194. One of known methods for preparing this compound comprises reacting an α-olefin with β-mercaptopropionic acid or its ester and then reacting the resulting 3-alkylthiopropionic acid with pentaerythritol as taught in Japanese Patent Laid-Open Application No. 59225/79 and Japanese Patent Publication Nos. 39249/80 and 41654/80. However, this process produces not only n-alkyl compounds but also iso-alkyl compounds. Mixtures containing the isoalkyl compounds have greatly lowered melting points and require an increased cost for separation of the n-alkyl compounds.

U.S. Pat. No. 3,758,549 also discloses a process for preparing 3-alkylthiopropionic acid esters starting with alkylmercaptans. In this patent, however, there is only one specific example wherein ethylene glycol was used for esterification. A reference to pentaerythritol-tetrakis(3-n-dodecylthiopropionate), one of pentaerythritol-tetrakis(3-alkylthio-propionate), is found therein, but the information obtained from this reference is merely that this specific ester has a melting point of from 47° to 49° C.

SUMMARY OF THE INVENTION

One object of this invention is to provide a process for preparing a pentaerythritol-tetrakis(3-alkylthio-propionate), in which all of the four hydroxyl groups of pentaerythritol is esterified, in high yields at high purities starting with an alkylmercaptan.

It has now been discovered that the above object can be attained by a process for preparing a pentaerythritol-tetrakis(3-alkylthio-propionate) represented by the general formula:

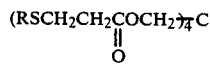

wherein R represents an alkyl group having from 8 to 30 carbon atoms, which comprises reacting an alkylmercaptan having from 8 to 30 carbon atoms with an acrylic ester or an acrylic amide to form a 3-alkylthio-propionic acid ester or a 3-alkylthio-propionic acid amide, hydrolyzing the ester or amide to form a 3-alkylthio-propionic acid, and then reacting this product with pentaerythritol.

BRIEF DESCRIPTION OF THE ACCOMPANYING DRAWING

The accompanying drawing is a flow sheet illustrating an embodiment of the present invention. In this drawing, each of $A^1$ to $A^5$ is a reactor; B is a condenser; C is a filter; D is a crystallization vessel; E is a centrifugal separator; F is a distillator; and G is a drier.

DETAILED DESCRIPTION OF THE INVENTION

According to the process of this invention, an alkylmercaptan having from 8 to 30 carbon atoms is reacted with an acrylic ester or an acrylic amide in the presence of an alkali catalyst to prepare a 3-alkylthio-propionic acid ester or a 3-alkylthio-propionic acid amide. The resulting ester or amide is then subjected to hydrolysis to obtain a 3-alkylthio-propionic acid. The starting acrylic ester preferably includes lower alkyl esters, such as a methyl ester, an ethyl ester, etc.

Although 3-alkylthio-propionic acids may be obtained through reactions using acrylonitrile in place of the acrylic ester or amide, followed by hydrolysis, use of the acrylic ester or amide is preferred in view of hydrolysis reactivity and yield of the 3-alkylthio-propionic acids, and particularly use of the acrylic amide is preferred.

The above-described addition reaction or hydrolysis may be effected in the absence of a solvent, but is preferably carried out in the presence of an inert solvent, such as benzene, toluene, xylene, and the like, as reaction solvent.

The alkali catalysts to be used in the addition reaction include sodium methylate, sodium hydroxide, potassium hydroxide, etc. The acrylic amide or ester is preferably used in a slight excess over an equivalent molar ratio to the alkylmercaptan, and more preferably at a molar ratio to the alkylmercaptan of 1.005 to 1.1. The reaction solvent, though not essential, taking toluene as an example, is preferably used at a weight ratio to the alkyl mercaptan of from 2/1 to 1/2.

The addition reaction can be carried out by heating a mixture of an alkylmercaptan, an alkali catalyst, e.g., sodium hydroxide, etc., and a reaction solvent, e.g., toluene, etc., to a prescribed temperature, preferably to a temperature of from 60° to 95° C., adding an aqueous solution of an acrylic amide or ester dropwise thereto with stirring, followed by allowing the mixture to react at that temperature for a prescribed period of time. The time required for the dropwise addition of the acrylic amide or ester is important for controlling a reaction-temperature and usually ranges from about 3 to about 5 hours, though varying depending on the cooling capacity of the reactor, and the like. The reaction time after the dropwise addition is preferably from about 2 to about 4 hours. The catalyst, taking sodium hydroxide as an example, is used in an amount of from 0.2 to 2.0% by weight, and preferably from 0.5 to 1.0% by weight, based on the alkylmercaptan.

The hydrolysis of the addition reaction mixture is carried out by adding an aqueous solution of an acid catalyst, e.g., hydrochloric acid, sulfuric acid, etc., as hydrolysis catalyst to the mixture and heating the mixture at a temperature of from 80° to 120° C. preferably in the copresence of the reaction solvent used in the addition reaction (e.g., toluene, benzene, etc.) which functions as an azeotropic agent. The amount of the catalyst is from 0.6 to 3.0 mols, and preferably from 1.0 to 2.0 mols, per mol of the 3-alkylthio-propionic acid amide or ester in the case of using sulfuric acid (62.5%) and from 1.2 to 3.0 mols, and preferably from 1.5 to 2.5 mols, per mol of the acid amide or ester in the case of using hydrochloric acid.

If desired, the hydrolysis system may contain a surface active agent for the purpose of ensuring smooth progress of the hydrolysis. The surface active agents to be used include those commonly employed in industry, with sodium alkylbenzenesulfonates, quaternary ammonium salts and the like being particularly preferred. The amount of the surface active agent to be added is not more than 1.5% by weight, and preferably of from 0.5 to 1.0% by weight, based on the 3-alkylthio-propionic acid amide or ester. When sulfuric acid is used as a catalyst, the surface active agent addition effect is particularly noticeable.

The hydrolysis reaction is usually conducted for a period of from about 8 to about 20 hours. Since the rate of hydrolysis is reduced with time due to reduction in acid catalyst concentration, it is desirable to shorten the reaction time required by exchanging the acid catalyst by fresh one in an appropriate state during the reaction. For example, in the hydrolysis in the presence of a sulfuric acid having a concentration of from about 50 to about 70% by weight as catalyst, a first exchange of the catalyst is made at the point when 3 to 4 hours have elapsed from the commencement of hydrolysis, i.e., when the rate of hydrolysis has reached 60 to 70%, and a second exchange is made when the rate of hydrolysis has reached about 90%. The exchange of the sulfuric acid catalyst can be performed by allowing the reaction mixture to stand, withdrawing the thus separated sulfuric acid layer out of the system, and adding a fresh sulfuric acid catalyst to the system. The sulfuric acid to be added in exchange preferably has a concentration of from about 50 to about 70% by weight.

The above-described hydrolysis reaction is very important and should be conducted sufficiently. Insufficient hydrolysis causes various operating problems in the subsequent esterification, crystallization or filtration step.

After completion of the hydrolysis, the reaction mixture is washed with water or hot water to remove the unreacted materials, inorganic salts, catalysts, surface active agents, etc. The number of times of washing depends on conditions, such as the amount of water used, the temperature, whether stirring is combined or not, and the like and is, therefore selected so that the aqueous phase after washing may be substantially neutral in pH.

The thus prepared 3-alkylthio-propionic acid is then completely esterified with pentaerythritol. Prior to the esterification, the reaction solvent (e.g. toluene, etc.) used in the preceding steps may be removed, though not essential. The 3-alkylthio-propionic acid is preferably used in an amount of from 4.0 to 4.4 mols per mol of pentaerythritol. Mixing ratios of these reactants out of the above-recited range results in disadvantages, such as an increased proportion of either reactant remaining unreacted, a reduced yield of the desired tetrakis-ester compound, etc.

Catalysts which can be used in the esterification include acid catalysts commonly employed for this purpose, such as sulfuric acid, sulfonic acids, e.g., toluenesulfonic acid, benzenesulfonic acid, etc., strongly acidic ion-exchange resins, and the like, with p-toluenesulfonic acid being most preferred. The amount of p-toluenesulfonic acid to be used is from 0.2 to 5% by weight, and preferably from 2 to 3% by weight, based on the alkylthiopropionic acid.

Since the esterification is a reversible reaction, it is important to remove produced water out of the system in order to ensure smooth progress of the reaction. To this effect, the reaction is preferably performed in the presence of an azeotropic agent, such as toluene, benzene, etc., under conditions allowing distillation of an azeotropic mixture formed by water and the azeotropic agent. In the case where toluene, benzene, etc., is used as a reaction solvent in the preceding steps, the remaining solvent may serve as azeotropic agent. The azeotropy can be carried out preferably at a temperature ranging from 100° to 140° C. under atmospheric pressure or, rather preferably, under slightly reduced pressure.

Completion of the esterification may be confirmed through ceasing from distillation of water, but is usually confirmed to advantage by a method, in which the reaction mixture is taken out and subjected to liquid chromatography to observe disappearance of the tris compound. After completion of the esterification, the reaction mixture is washed successively with an alkali and water or hot water to remove the catalyst completely.

The reaction solvent (e.g., toluene, etc.) present in the resulting reaction mixture is removed by, for example, distillation under reduced pressure, etc. to thereby obtain a crude pentaerythritol-tetrakis(3-alkylthio-propionate).

The resulting crude product is then recrystallized from isopropanol or a mixed solvent consisting mainly of isopropanol, such as a mixture containing not less than 50% by weight of isopropanol and methanol, ethanol, butanol, or the like. The amount of the recrystallizing solvent, taking isopropanol for an instance, is from twice to triple the amount of the crude product. The recrystallization can be carried out by dissolving the crude product in the above-described solvent at a temperature of from 30° to 75° C., followed by cooling to a temperature of 30° C. or lower, preferably of from 5° to 25° C. The crude product subject to recrystallization should be dehydrated sufficiently because insufficient dehydration of the crude product hinders crystallization.

When products of high whiteness are desired, such can be accomplished by adding an activated carbon powder to the crude product solution to effect decoloration, removing the activated carbon by filtration, and then crystallizing the filtrate.

The crystals thus precipitated are separated from the mother liquor by means of a centrifugal separator or the like and, if necessary, washed with a solvent, such as isopropanol, etc. The mother liquor and the washing are subjected to distillation to recover the solvent. The residue on distillation can be utilized by recycling to the esterification step, as it still contains considerable amounts of the purposed compound as well as the 3-alkylthio-propionic acid, and the like. It is also possible that pentaerythritol is added to the residue after solvent recovery to effect esterification and the reaction mixture is processed in the same manner as described above to obtain the final product.

The crystals thus separated are then dried to give the desired compound. The drying is preferably carried out by a fluid process, particularly without heating.

An embodiment of the present invention will be illustrated below by way of the accompanying drawing (flow sheet), in which an apparatus to be used for carrying out the process of the invention is schematically shown.

A predetermined amount of a starting alkylmercaptan is fed through pipe 1 into reactor $A^1$, in which a predetermined amount of toluene as reaction solvent has been charged through pipe 2. The mixture in reactor $A^1$ is heated to 75° to 85° C. while introducing $N_2$ gas therein through pipe 4. Then, a 40 wt % aqueous solution of acrylic amide is added thereto dropwise through pipe 3 to effect reaction while controlling the inner temperature of reactor $A^1$ between 80° and 85° C. After completion of the dropwise addition of the acrylic amide aqueous solution, the reaction is continued at the same temperature as above for a predetermined time. The overall reaction in reactor $A^1$ is under stirring. By this reaction, there is obtained a 3-alkylthio-propionic acid amide.

The reaction mixture in reactor $A^1$ is transferred to reactor $A^2$ through pipe 5, and a predetermined amount of sulfuric acid is fed therein through pipe 6. The mixture is heated at about 100° C. while stirring to effect hydrolysis. If desired, a surface active agent, e.g., sodium alkylbenzenesulfonates, can be added to the reaction system through pipe 7. After 2 to 3 hours from the commencement of the reaction, the stirring is once stopped to allow the reaction mixture to stand, and the sulfuric acid layer thus separated is withdrawn. After a predetermined amount of fresh sulfuric acid is added to reactor $A^2$ through pipe 6, the reaction is further continued under the same conditions as above. It is possible to substitute reactor $A^1$ for reactor $A^2$.

The reaction mixture in reactor $A^2$ is transferred to reactor $A^3$ through pipe 8, and water or hot water is supplied therein through pipe 9 to conduct washing. It is possible to substitute reactor $A^3$ by reactor $A^1$ or $A^2$.

The reaction mixture in reactor $A^3$ is then transferred to reactor $A^4$ through pipe 10, and a predetermined amount of pentaerythritol is fed thereto through pipe 11. Into reactor $A^4$, a residue on distillation after solvent recovery from the crystallization mother liquor hereinafter described may be recycled through pipe 13. A predetermined amount of an esterification catalyst, e.g., p-toluenesulfonic acid, is fed to reactor $A^4$ through pipe 12, and the mixture is allowed to react at reflux while heating at 100° to 135° C. with stirring. During this reaction, vapors evolved from reactor $A^4$, e.g., an azeotropic mixture of toluene and water, reaches condenser B through pipe 14. Water condensed in condenser B is discharged from the system through pipe 14'', and condensed toluene is recycled to reactor $A^4$ through pipe 14'. The end point of this esterification is determined by appropriately sampling the reaction mixture, analyzing it by liquid chromatography and confirming disappearance of the tris compound.

The reaction mixture in reactor $A^4$ after completion of the esterification reaction is transferred to reactor $A^5$ through pipe 15. Water or hot water is supplied therein through pipe 16 to effect washing, and the washing is withdrawn through pipe 18. After the inner pressure of reactor $A^5$ is reduced to about 100 mmHg, the reaction solvent, e.g., toluene, is removed by distillation.

A predetermined amount of isopropanol or a mixed solvent consisting mainly of isopropanol is added to reactor $A^5$ through pipe 16, followed by heating at 30° to 75° C. while stirring to dissolve the mixture. Further, a predetermined amount of an activated carbon powder is fed thereto through pipe 17 for decoloration, and the mixture is stirred for a predetermined period of time. The mixture in reactor $A^5$ is then forwarded to filter C through pipe 19, where the activated carbon is separated. The filtrate is transferred to crystallization vessel D. It is possible to substitute reactor $A^5$ with reactor $A^4$.

The solution in crystallization vessel D is cooled to a temperature of from 5° to 30° C. to thereby precipitate crystals of a pentaerythritol-tetrakis(3-alkylthio-propionate). The time required for crystallization is usually from 3 to 5 hours. The crystals thus precipitated in crystallization vessel D is introduced to centrifugal separator E through pipe 20 together with the mother liquor, wherein the crystals are separated. The separated crystals are dried in drier G and taken out as a final product. The mother liquor separated in centrifugal separator E is introduced to distillator F through pipe 21, and the solvent, e.g., isopropanol, etc., is recovered through pipe 22. Since the residue after recovery of the solvent contains the starting 3-alkylthio-propionic acid, tris-ester compound, and the like it can be recycled to reactor $A^4$ through pipe 13 as described above. It is also possible that the residue in distillator F is reacted with pentaerythritol separately fed and the resulting mixture is processed in the same manner as described above to obtain a final product.

This invention will now be illustrated in greater detail with reference to the following examples, but it should be understood that they are not intended to limit the present invention.

EXAMPLE 1

In a 5 l-volume three-necked flask equipped with a stirrer was charged a mixture of 808 g of dodecylmercaptan, 86 g of sodium hydroxide and 620 g of toluene, and the mixture was heated to 80° C. A 40 wt % aqueous solution containing 287 g of acrylic amide was added thereto dropwise over a period of 4 hours while maintaining the inner temperature at 80°±5° C. under stirring. After the dropwise addition, the reaction was continued for an additional 3 hours under stirring while maintaining the liquid temperature at 85° C.

To the reaction mixture were added 360 ml of 62.5 wt % sulfuric acid and 8 g of sodium dodecylbenzenesulfonate, followed by heating at 100° C. with stirring for 20 hours. After completion of the reaction, the oily matter was separated and washed five times with 1,000 ml portions of hot water at 70° C.

To the oily product after washing were added 130 g of pentaerythritol and 24 g of p-toluenesulfonic acid, and the mixture was allowed to react by heating at a temperature of from 100° to 130° C. while dehydrating under azeotropic refluxing for a period of 24 hours. After completion of the reaction, the reaction product was cooled to room temperature, washed three times with 1,000 ml portions of hot water at 70° C. and distilled to recover toluene. To the residue was added 2,900 g of isopropanol, followed by heating to 70° C. to dissolve. The solution was cooled to 20° C., at which it was kept for 12 hours. The crystals precipitated were separated by filtration and dried in a fluidized bed using air at room temperature to obtain 1,093 g of a product having a melting point of 51.2° to 51.9° C. Liquid chromatography (column: Fine-pack-Gel, produced by Nippon Bunko K.K.) of the product revealed that the purity of pentaerythritol-tetrakis(3-n-dodecylthio-propionate) was 99.7%. The yield of the product based on the starting dodecyl mercaptan was 75%.

EXAMPLE 2

Pentaerythritol-tetrakis(3-n-dodecylthio-propionate) was prepared in the same manner as described in Example 1, except for using 287 g of methyl acrylate in place of 287 g of acrylic amide as used in Example 1. The yield of the product based on the starting dodecyl mercaptan was found to be 72%.

As described above, a pentaerythritol-tetrakis(3-alkylthio-propionate) can easily be prepared from an alkyl mercaptan at high purity and in high yield by the process according to the present invention.

While the invention has been described in detail and with reference to specific embodiments thereof, it will be apparent to one skilled in the art that various changes and modifications can be made therein without departing from the spirit and scope thereof.

What is claimed is:

1. A process for preparing a pentaerythritol-tetrakis(3-alkylthio-propionate) having the formula:

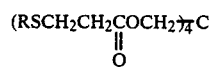

wherein R is an alkyl group having from 8 to 30 carbon atoms, which comprises:
   (a) reacting an alkylmercaptan having from 8 to 30 carbon atoms with an acrylic amide in the presence of an alkali catalyst at a temperature of from 60° to 95° C. to form a 3-alkylthiopropionate acid amide;
   (b) hydrolyzing the amide to form a 3-alkylthio-propionic acid in the presence of an acid catalyst; and
   (c) reacting the 3-alkylthiopropionic acid with pentaerythritol.

2. The process as claimed in claim 1, wherein the reaction between the alkylmercaptan and the acrylic amide is carried out in an inert solvent.

3. The process as claimed in claim 1, wherein said acrylic amide is used at a molar ratio of from 1.005 to 1.1 based on the alkylmercaptan.

4. The process as claimed in claim 1, wherein the hydrolysis of the 3-alkylthio-propionic acid amide is carried out in the presence of an acid catalyst at a temperature of from 80° to 120° C.

5. The process as claimed in claim 1, wherein the hydrolysis of the 3-alkylthio-propionic acid amide is carried out in a reaction solvent.

6. The process as claimed in claim 4, wherein said acid catalyst is exchanged with a fresh acid catalyst at least once during the reaction.

7. The process as claimed in claim 1, wherein the reaction between the 3-alkylthio-propionic acid and pentaerythritol is carried out in the presence of an acid catalyst at a temperature of from 100° to 140° C.

8. The process as claimed in claim 1, wherein the 3-alkylthio-propionic acid is used in an amount of from 4.0 to 4.4 mols per mol of pentaerythritol.

9. The process as claimed in claim 7, wherein the reaction is carried out in the presence of an azeotropic agent while removing produced water as an azeotropic mixture.

10. The process as claimed in claim 1, wherein the process further includes recrystallization of the pentaerythritoltetrakis(3-alkylthio-propionate) from isopropanol or a mixed solvent consisting mainly of isopropanol.

11. The process as claimed in claim 1, wherein said alkali catalyst is selected from the group consisting of sodium methylate, sodium hydroxide and potassium hydroxide.

12. The process as claimed in claim 1, wherein said acrylic amide is reacted with the alkylmercaptan by adding the amide dropwise to the alkylmercaptan over a period of about 3 to 5 hours.

13. The process as claimed in claim 1, wherein the catalyst in step (a) is used in an amount of from 0.2 to 2.0% by weight based on the alkylmercaptan.

14. The process as claimed in claim 4, wherein said acid catalyst is used in the amount of from 0.6 to 3.0 moles per mole of 3-alkylthiopropionic acid amide.

15. The process as claimed in claim 4, wherein said hydrolysis is further effected in the presence of a surface active agent.

16. The process as claimed in claim 15, wherein said surface active agent is a sodium alkylbenzenesulfonate or a quaternary ammonium salt used in the amount of up to about 1.5% by weight.

17. The process is claimed in claim 1, wherein said hydrolysis is conducted for about 8 to 20 hours.

18. The process as claimed in claim 17, wherein a first exchange of fresh catalyst is made after attaining a rate of hydrolysis of about 60–70%, and a second exchange of fresh catalyst is made after attaining a rate of hydrolysis of about 90%.

19. The process as claimed in claim 1, wherein said acid catalyst is hydrochloric acid or sulfuric acid.

* * * * *